(12) United States Patent
Nariyuki et al.

(10) Patent No.: US 8,946,644 B2
(45) Date of Patent: Feb. 3, 2015

(54) RADIATION DETECTOR, METHOD OF MANUFACTURING RADIATION DETECTOR, AND RADIOGRAPHIC IMAGE CAPTURING APPARATUS INCORPORATING RADIATION DETECTOR

(75) Inventors: Fumito Nariyuki, Kanagawa-ken (JP);
Toshitaka Agano, Kanagawa-ken (JP);
Yasunori Ohta, Kanagawa-ken (JP);
Haruyasu Nakatsugawa,
Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 652 days.

(21) Appl. No.: 13/306,502

(22) Filed: Nov. 29, 2011

(65) Prior Publication Data
US 2012/0153171 A1 Jun. 21, 2012

(30) Foreign Application Priority Data

Dec. 20, 2010 (JP) .................................. 2010-282566
Nov. 4, 2011 (JP) .................................. 2011-242194

(51) Int. Cl.
*G01T 1/20* (2006.01)
*A61B 6/00* (2006.01)

(52) U.S. Cl.
CPC ............. *G01T 1/2018* (2013.01); *A61B 6/4233* (2013.01)
USPC ........................................................ 250/369

(58) Field of Classification Search
CPC ........................................................ G01T 1/20
USPC ........................................................ 250/369
See application file for complete search history.

(56) References Cited

U.S. PATENT DOCUMENTS

| 7,629,587 B2 | 12/2009 | Yagi et al. |
| 2001/0025934 A1 | 10/2001 | Agano |
| 2003/0132385 A1 | 7/2003 | Agano |

(Continued)

FOREIGN PATENT DOCUMENTS

| CN | 101772714 A | 7/2010 |
| CN | 101903801 A | 12/2010 |

(Continued)

OTHER PUBLICATIONS

The first Office Action issued by the Chinese Patent Office on Jul. 18, 2014, which corresponds to Chinese Patent Application No. 201110387989.2 and is related to U.S. Appl. No. 13/306,502; with English language translation.

(Continued)

*Primary Examiner* — David Porta
*Assistant Examiner* — Faye Boosalis
(74) *Attorney, Agent, or Firm* — Studebaker & Brackett PC

(57) ABSTRACT

A radiographic image capturing apparatus includes a housing and a radiation detector accommodated in the housing. The radiation detector includes a scintillator for converting radiation into visible light and photodiodes for converting the visible light into electric charges. If it is assumed that a temperature-dependent rate of change in sensitivity of the scintillator with respect to the radiation is represented by A [%/K] and a temperature-dependent rate of change in sensitivity of the photodiodes with respect to visible light is represented by B [%/K], a scintillator and photodiodes are selected having temperature-dependent rates of change A and B that satisfy the following inequality (1):

$$-0.35\ [\%/K] < A+B < 0.35\ [\%/K] \qquad (1).$$

18 Claims, 9 Drawing Sheets

(56) References Cited

U.S. PATENT DOCUMENTS

| | | |
|---|---|---|
| 2004/0021082 A1 | 2/2004 | Wong et al. |
| 2005/0253097 A1 | 11/2005 | Agano |
| 2010/0012846 A1 | 1/2010 | Wang |
| 2010/0264322 A1 | 10/2010 | Levene et al. |
| 2012/0001076 A1 | 1/2012 | Chappo et al. |
| 2013/0292575 A1 | 11/2013 | Chappo et al. |

FOREIGN PATENT DOCUMENTS

| | | | |
|---|---|---|---|
| JP | 55142261 A | * 11/1980 | ............ G01T 1/208 |
| JP | 63-243782 | 10/1988 | |
| JP | 2001-281345 A | 10/2001 | |
| JP | 2003-209232 A | 7/2003 | |
| JP | 2007-222604 A | 9/2007 | |
| WO | 2010/109353 A2 | 9/2010 | |

OTHER PUBLICATIONS

Chen et al.; "Temperature Effects of CsI(Tl) Crystal Detector with APD Readout"; High Energy Physics and Nuclear Physics; Aug. 2007; pp. 760-763; vol. 31, No. 8; China.

An Office Action; "Rejection of the Application," issued by the Japanese Patent Office on Aug. 26, 2014, which corresponds to Japanese Patent Application No. 2011-242194 and is related to U.S. Appl. No. 13/306,502; with English language partial translation.

* cited by examiner

FIG. 9

| | SCINTILLATOR COMPOSITION | EVAPORANT TEMPERATURE UPON SCINTILLATOR FILM GROWTH [°C] | TEMPERATURE-DEPENDENT RATE OF CHANGE A IN SCINTILLATOR SENSITIVITY [%/K] | TEMPERATURE-DEPENDENT RATE OF CHANGE B IN PHOTODIODE SENSITIVITY [%/K] | A+B | DENSITY DIFFERENCE VISUAL RECOGNIZABILITY AT 25°C, 35°C | BUMP-INDUCED IMAGE DEFECTS |
|---|---|---|---|---|---|---|---|
| INVENTIVE EXAMPLE 1 | CsI:Tl | 750 | −0.19 | +0.51 | +0.32 | ○ | ○ |
| INVENTIVE EXAMPLE 2 | CsI:Tl | 800 | −0.22 | +0.51 | +0.29 | ○ | ○ |
| INVENTIVE EXAMPLE 3 | CsI:Tl | 900 | −0.34 | +0.51 | +0.17 | ○ | ○ |
| INVENTIVE EXAMPLE 4 | CsI:Tl | 950 | −0.37 | +0.51 | +0.14 | ○ | △ |
| COMPARATIVE EXAMPLE 1 | CsI:Tl | 700 | −0.12 | +0.51 | +0.39 | △ | ○ |
| COMPARATIVE EXAMPLE 2 | GOS | − | −0.03 | +0.51 | +0.48 | △ | ○ | ically is healthy, then the artifact may possibly cause the observer to erroneously recognize the body region as an affected area, and hence the artifact may lower the diagnostic accuracy based on the image.

RADIATION DETECTOR, METHOD OF MANUFACTURING RADIATION DETECTOR, AND RADIOGRAPHIC IMAGE CAPTURING APPARATUS INCORPORATING RADIATION DETECTOR

CROSS-REFERENCE TO RELATED APPLICATION

This application is based upon and claims the benefit of priority from Japanese Patent Applications No. 2010-282566 filed on Dec. 20, 2010 and No. 2011-242194 filed on Nov. 4, 2011, of which the contents are incorporated herein by reference.

BACKGROUND OF THE INVENTION

1. Field of the Invention

The present invention relates to a radiation detector having a scintillator for converting radiation into visible light and photodiodes for converting visible light into electric signals, a method of manufacturing a radiation detector, and a radiographic image capturing apparatus that incorporates a radiation detector therein.

2. Description of the Related Art

In the medical field, it has widely been customary to apply radiation from a radiation source to a subject, and to detect radiation that has passed through the subject with a radiographic image capturing apparatus, thereby capturing a radiographic image of the subject. The radiographic image capturing apparatus includes a scintillator for converting radiation that has passed through the subject into visible light, and a radiation detector having a photodetector substrate which includes photodiodes for converting the visible light into electric charges. The radiographic image of the subject is generated based on the electric charges generated by the photodiodes.

SUMMARY OF THE INVENTION

Radiographic images of the type described above may have so-called artifacts, which appear as the temperature rises. It is believed that such artifacts are developed in a radiographic image because the characteristics of semiconductors that make up pixels included in a radiation detector and a signal processing circuit tend to vary due to the rise in temperature, as disclosed in Japanese Laid-Open Patent Publication No. 2007-222604. A study conducted by the applicant of the present invention shows that even upon an increase in temperature, if a deviation in the temperature distribution in an image capturing area of the radiation detector, i.e., a temperature difference at each location in the radiation detector, is small, then no significant problem arises, but artifacts may appear with relative ease if the temperature distribution suffers a large deviation. The tendency manifests itself in particular if the sensitivity of the semiconductors varies with temperature.

If an artifact appears in the image of a body region that actually is healthy, then the artifact may possibly cause the observer to erroneously recognize the body region as an affected area, and hence the artifact may lower the diagnostic accuracy based on the image.

Various attempts have heretofore been made in the art to prevent artifacts from appearing in radiographic images. For example, Japanese Laid-Open Patent Publication No. 2007-222604 discloses a radiographic image capturing apparatus including a heat radiator, which discharges heat generated by the radiation detector for thereby preventing the temperature from increasing.

Japanese Laid-Open Patent Publication No. 63-243782 discloses a technique for correcting radiation data obtained by a radiation detector based on the temperature at a time that the radiation detector detects the radiation data, in view of a gain variation caused by a change in the temperature of a scintillator.

The radiographic image capturing apparatus disclosed in Japanese Laid-Open Patent Publication No. 2007-222604 requires a heat radiator. Therefore, the disclosed radiographic image capturing apparatus includes an increased number of parts, is complex in structure, heavy, and is costly to manufacture.

The heat radiator can lower the maximum temperature in the radiographic image capturing apparatus. However, the heat radiator tends to cause a temperature difference between a region, which is spaced from the heat radiator and hence is difficult to radiate heat therefrom, and a region, which is close to the heat radiator and from which heat can easily be radiated. The temperature difference, or stated otherwise, the deviation in the temperature distribution of the radiographic image capturing apparatus, is liable to generate artifacts in radiographic images captured by the radiographic image capturing apparatus, because semiconductors manifest different characteristics in high-temperature and low-temperature regions respectively.

The radiation data correcting technique disclosed in Japanese Laid-Open Patent Publication No. 63-243782 requires the manufacturer to perform a complicated task for generating a corrective program. Furthermore, the disclosed radiation data correcting technique requires a complex system arrangement, since it requires a control circuit for executing the correcting program.

In addition, an artifact that is generated due to a deviation in the temperature distribution may not necessarily be corrected, since the deviation in the temperature distribution is time-dependent. Further, since a variation in sensitivity of the radiation detector, which is caused by a deviation in the temperature distribution, is recognized only if the radiation detector is irradiated with radiation, or stated otherwise, since such a variation cannot be recognized until the radiation detector is irradiated with radiation, the artifact may not necessarily be corrected from an offset image.

It is a general object of the present invention to provide a radiation detector, which is made up of a relatively small number of parts and hence is simple in structure.

A major object of the present invention is to provide a radiation detector, which in particular does not require a correcting program.

Another object of the present invention is to provide a radiation detector, which is capable of effectively preventing artifacts from being developed.

Still another object of the present invention is to provide a method of manufacturing such a radiation detector.

Yet another object of the present invention is to provide a radiographic image capturing apparatus, which incorporates such a radiation detector therein.

The above objects can be achieved by arrangements [1] through [4] below.

[1] A radiation detector comprising a scintillator for converting radiation into visible light and photodiodes for converting the visible light into electric charges, wherein:

if it is assumed that a temperature-dependent rate of change in sensitivity of the scintillator with respect to the radiation is represented by A [%/K] and a temperature-dependent rate of change in sensitivity of the photodiodes with respect to visible light is represented by B [%/K], the temperature-dependent rates of change A and B satisfy the following inequality (1):

$$-0.35\ [\%/K] < A+B < 0.35\ [\%/K] \quad (1)$$

[2] A method of manufacturing a radiation detector including a scintillator for converting radiation into visible light and photodiodes for converting the visible light into electric charges, comprising the steps of:

measuring a temperature-dependent rate of change in sensitivity of the scintillator with respect to the radiation; and if it is assumed that the temperature-dependent rate of change in sensitivity of the scintillator with respect to the radiation is represented by A [%/K], selecting, as the photodiodes, photodiodes having a temperature-dependent rate of change B [%/K] in sensitivity with respect to the visible light that satisfies the following inequality (1):

$$-0.35\ [\%/K] < A+B < 0.35\ [\%/K] \quad (1)$$

[3] A method of manufacturing a radiation detector including a scintillator for converting radiation into visible light and photodiodes for converting the visible light into electric charges, comprising the steps of:

measuring a temperature-dependent rate of change in sensitivity of the photodiodes with respect to the visible light; and if it is assumed that the temperature-dependent rate of change in sensitivity of the photodiodes with respect to the visible light is represented by B [%/K], selecting, as the scintillator, a scintillator having a temperature-dependent rate of change A [%/K] in sensitivity with respect to the radiation that satisfies the following inequality (1):

$$-0.35\ [\%/K] < A+B < 0.35\ [\%/K] \quad (1)$$

[4] A radiographic image capturing apparatus comprising a housing and a radiation detector accommodated in the housing, the radiation detector including a scintillator for converting radiation into visible light and photodiodes for converting the visible light into electric charges, wherein:

the housing has an irradiated surface facing a radiation source;

if it is assumed that a temperature-dependent rate of change in sensitivity of the scintillator with respect to the radiation is represented by A [%/K] and a temperature-dependent rate of change in sensitivity of the photodiodes with respect to visible light is represented by B [%/K], the temperature-dependent rates of change A and B satisfy the following inequality (1):

$$-0.35\ [\%/K] < A+B < 0.35\ [\%/K] \quad (1)$$

and the radiation detector is mounted on a surface of the housing that is opposite to the irradiated surface.

According to the present invention, a scintillator and photodiodes are selected such that the sum of the temperature-dependent rates of change in sensitivity of the scintillator and the photodiodes falls within a predetermined numerical range. Therefore, the temperature dependencies in sensitivity of the scintillator and the photodiodes cancel each other out. Since the photodiodes generate an amount of electric charge depending on the amount of radiation that passes through the subject, artifacts are effectively prevented from being developed in the captured radiographic image, and hence diagnostic accuracy based on the captured radiographic image is prevented from being lowered.

Inasmuch as temperature dependencies in sensitivity of the scintillator and the photodiodes cancel each other out, even if a temperature distribution of the radiation detector suffers from deviations, artifacts are prevented from being developed in the captured radiographic image due to such deviations in the temperature distribution. Accordingly, the radiation detector does not require a heat radiator, and there is no need for a correcting program for reducing artifacts that may be developed in the captured radiographic image. Therefore, the radiation detector can be relatively simple in structure.

The temperature-dependent rates of change A and B in sensitivity of the scintillator and the photodiodes may be measured before the scintillator and the photodiodes are combined with each other. If a scintillator having a certain temperature-dependent rate of change A in sensitivity is selected, then photodiodes having a temperature-dependent rate of change B in sensitivity, which satisfies inequality (1), may be selected.

Conversely, if photodiodes having a certain temperature-dependent rate of change B in sensitivity are selected, then a scintillator having a temperature-dependent rate of change A in sensitivity, which satisfies inequality (1), may be selected.

The scintillator and the photodiodes having temperature-dependent rates of change A and B in sensitivity that satisfy inequality (1) may be made of CsI and amorphous silicon, respectively. CsI and amorphous silicon have respective temperature-dependent rates of change A and B in sensitivity, which satisfy inequality (1).

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 9 is a table showing temperature-dependent rates of change A and B in sensitivity of radiation detectors in electronic cassettes according to Inventive Examples 1 through 4 and Comparative Examples 1 and 2, together with evaluations of radiographic images captured thereby.

DESCRIPTION OF THE PREFERRED EMBODIMENTS

Radiation detectors and a method of manufacturing radiation detectors according to preferred embodiments of the present invention will be described in detail below with reference to the accompanying drawings, in connection with radiographic image capturing apparatus incorporating the radiation detectors therein.

Figure 1:
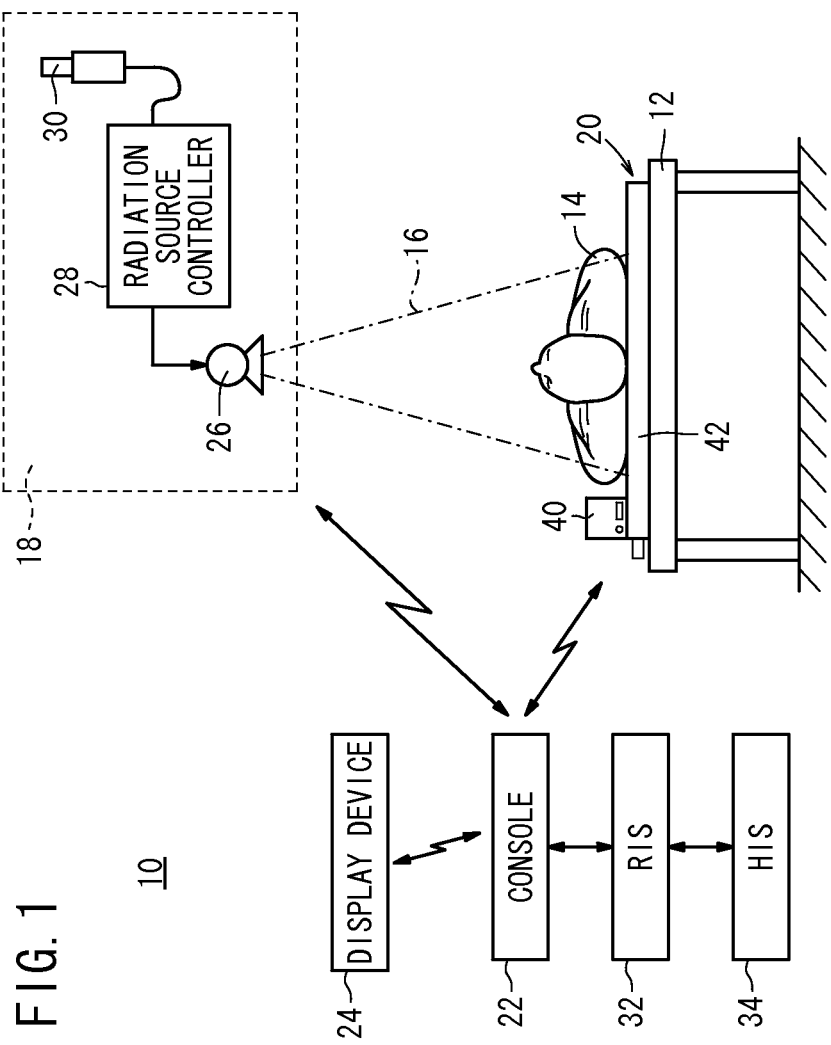
FIG. 1 is a schematic view, partially in block form, of a radiographic image capturing system incorporating a radiographic image capturing apparatus therein according to an embodiment of the present invention.

FIG. 1 is a schematic view, partially in block form, of a radiographic image capturing system 10 incorporating therein an electronic cassette (radiographic image capturing apparatus) 20 according to an embodiment of the present invention.

As shown in FIG. 1, the radiographic image capturing system 10 includes a radiation output device 18 for applying radiation 16 to a subject 14, such as a patient who lies on an image capturing base 12 such as a bed or the like, an electronic cassette (radiographic image capturing apparatus) 20 for detecting radiation 16 that has passed through the subject 14 and converting the detected radiation into a radiographic image, a console 22 for controlling the radiographic image capturing system 10 in its entirety and receiving input actions from a doctor or a radiological technician, and a display device 24 for displaying captured radiographic images, etc.

The radiation output device 18 includes a radiation source 26 for emitting radiation 16, a radiation source controller 28 for controlling the radiation source 26, and a radiation switch 30. The radiation source 26 applies radiation 16 to the subject 14 and the electronic cassette 20. Radiation 16 that is emitted from the radiation source 26 may be X-rays, $\alpha$-rays, $\beta$-rays, or $\gamma$-rays, an electron beam, or the like.

The radiation switch 30 can be pushed in two strokes, i.e., in a half stroke and a full stroke. If the radiation switch 30 is pushed in a half stroke by the doctor or radiological technician, a signal is sent to the radiation source controller 28 to prepare the radiation source 26 for emitting radiation 16. If the radiation switch 30 is subsequently pushed in a full stroke, a signal is sent to the radiation source controller 28 to enable the radiation source 26 to start emitting radiation 16.

The console 22 is connected to a radiology information system (RIS) 32, which generally manages radiographic image information handled by the radiological department of a hospital together with other information. The RIS 32 is connected to a hospital information system (HIS) 34, which generally manages medical information in the hospital.

The radiation output device 18, the electronic cassette 20, the console 22, and the display device 24 send and receive signals to and from each other by way of a wireless LAN according to standards such as UWB (Ultra-Wide Band), IEEE802.11.a/b/g/n. or the like, or wireless communications using milliwaves.

If the radiation switch 30 is pushed in a half stroke or a full stroke, the radiation output device 18 may send and receive signals. For example, if the radiation switch 30 is pushed in a half stroke by the doctor or radiological technician, the radiation output device 18 sends a signal to the console 22 indicative of preparing the radiation source 26 to emit radiation 16, and if the radiation switch 30 is pushed in a full stroke by the doctor or radiological technician, the radiation output device 18 sends a signal to the console 22 indicative of enabling the radiation source 26 to start emitting radiation 16.

Figure 2:
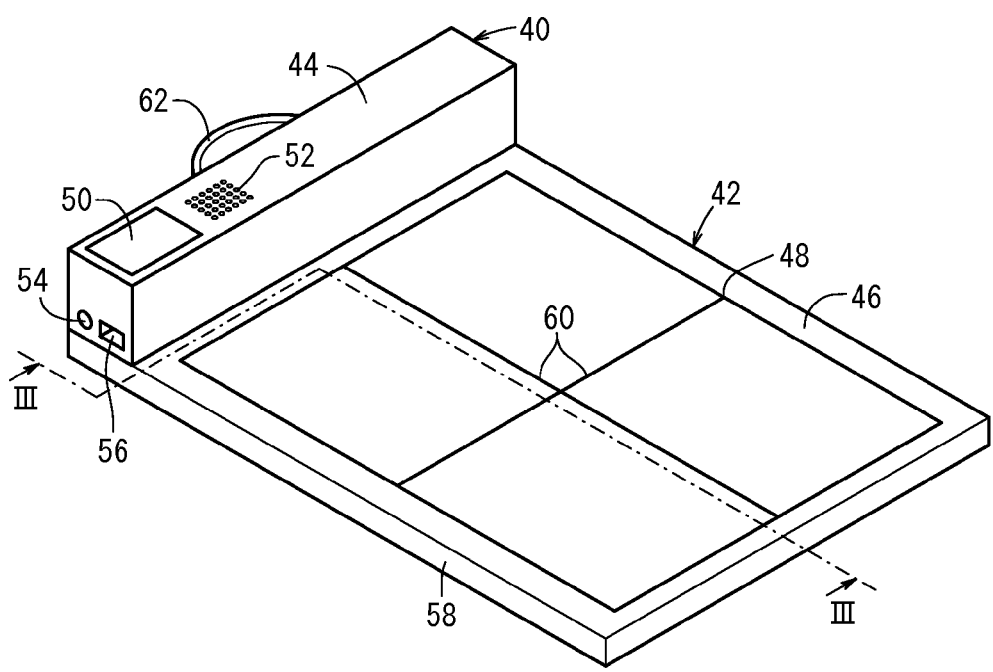
FIG. 2 is a perspective view of an electronic cassette, which serves as the radiographic image capturing apparatus shown in FIG. 1.

As shown in FIG. 2, the electronic cassette 20 has a controller 40 for controlling the electronic cassette 20 in its entirety, and a panel 42 for placement of the subject 14 thereon. The panel 42 is thinner than the controller 40.

The controller 40 includes a substantially rectangular housing 44 made of a material that is impermeable to radiation 16. The housing 44 extends along one end of an irradiated surface 46 of the panel 42. The controller 40 is disposed outside of an image capturing area 48 on the irradiated surface 46. On the upper surface of the housing 44, a display control panel 50 is provided in the form of a touch panel for the doctor or radiological technician to enter various items of information. A speaker 52 also is provided thereon for outputting sounds representing various notices for the doctor or radiological technician.

On a side surface of the housing 44, an AC adapter input terminal 54 is provided, which is supplied with charging electric power from an external power source. Further, a USB terminal 56 is provided thereon as an interface for sending and receiving information to and from an external device such as the console 22, for example.

The panel 42 includes a substantially rectangular housing 58 made of a material that is permeable to radiation 16. The irradiated surface 46 serves as an upper surface of the panel 42, which is irradiated with radiation 16. The irradiated surface 46 has guide lines 60 disposed substantially centrally thereon, which are indicative of an image capturing area and an image capturing position for the subject 14. The guide lines 60 include an outer frame representing an image capturing area 48, which indicates an irradiation field to be irradiated with radiation 16 on the irradiated surface 46. The guide lines 60 have a central position where the guide lines 60 cross each other in a crisscross pattern at a central position of the image capturing area 48.

The electronic cassette 20 also has a grip 62 on a side thereof close to the controller 40 for the doctor or radiological technician to hold. The doctor or radiological technician can hold the grip 62 and carry the electronic cassette 20 to a desired location, e.g., the image capturing base 12. Therefore, the electronic cassette 20 is a portable radiographic image capturing apparatus.

Figure 3:
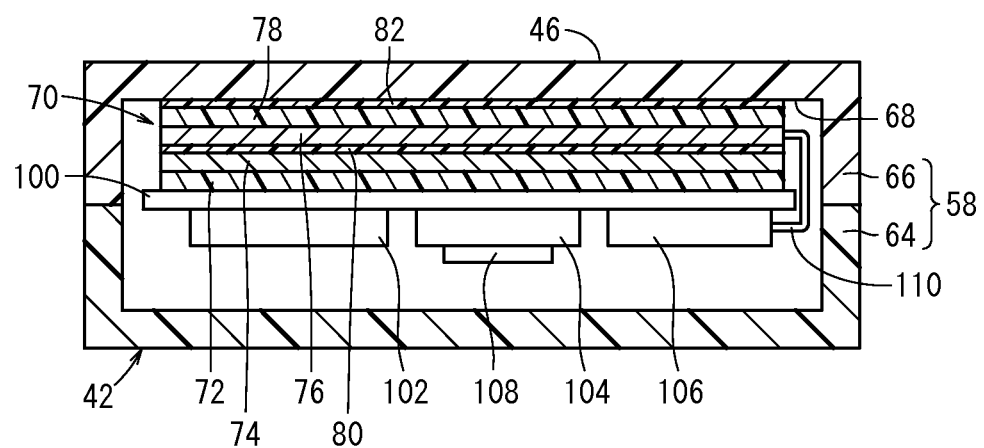
FIG. 3 is a cross-sectional view taken along line III-III of FIG. 2.

As shown in FIG. 3, the housing 58 includes a first casing 64 serving as a lower casing and a second casing 66 serving as an upper casing, which includes the irradiated surface 46. The housing 58 accommodates therein a radiation detector 70 for converting radiation 16 into a radiographic image. The radiation detector 70 is mounted on an inner ceiling surface 68 of the second casing 66, which is opposite to the irradiated surface 46.

Figure 4:
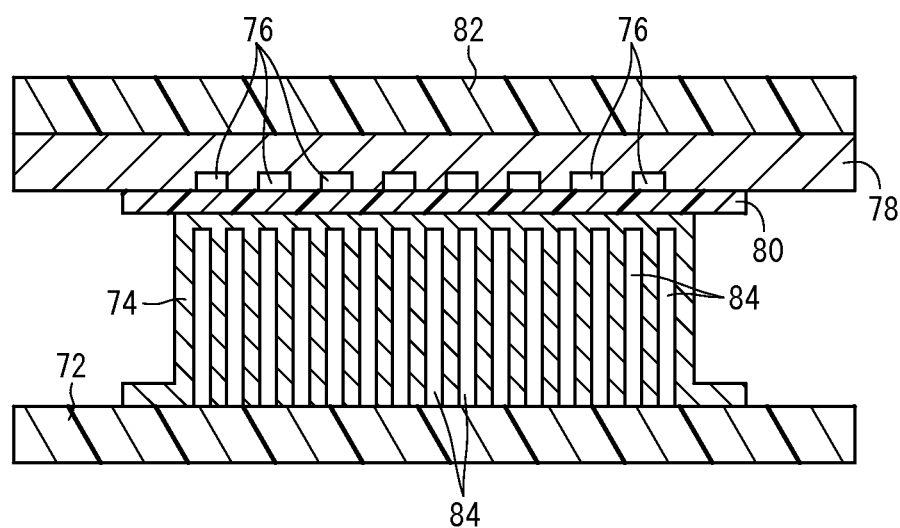
FIG. 4 is an enlarged cross-sectional view of a central portion of a radiation detector in the electronic cassette shown in FIG. 3.

As shown in FIG. 4, the radiation detector 70 includes a scintillator support board 72, a scintillator 74, and a photodetector substrate 78 having photodiodes 76, such elements being successively arranged in this order upwardly toward the inner ceiling surface 68. The scintillator 74 and the photodetector substrate 78 are joined to each other by a first bonding layer 80. The photodetector substrate 78, i.e., the radiation detector 70 itself, is joined to the inner ceiling surface 68 by a second bonding layer 82. The scintillator 74 has a columnar crystalline structure 84.

As shown in FIG. 3, the housing 58 also houses therein a circuit board support plate 100, which is joined to the radiation detector 70, for example.

The circuit board support plate 100 supports thereon a battery 102, a circuit board 104, and a charge amplifier IC 106, etc. The circuit board 104 includes a communication unit 108 for performing wireless or wired communications. The charge amplifier IC 106 is electrically connected to the photodiodes 76 through a flexible circuit 110.

Figure 5:
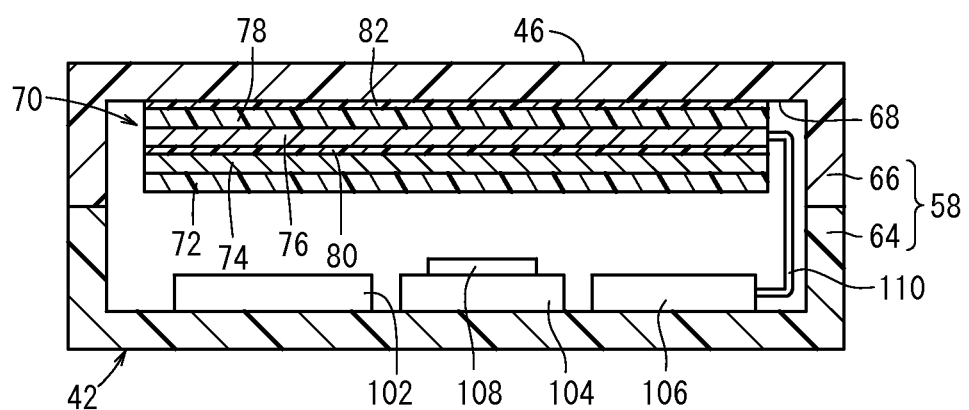
FIG. 5 is a cross-sectional view of an electronic cassette, which includes a circuit board, etc., disposed in a position different from the position shown in FIG. 3.

As shown in FIG. 5, the circuit board support plate 100 may be dispensed with, in which case the battery 102, the circuit board 104 (the communication unit 108), and the charge amplifier IC 106 are disposed in a position spaced from the radiation detector 70.

As is well known in the art, the scintillator 74 converts radiation 16 that has passed through the subject 14 into fluorescence, i.e., visible light. The photodiodes 76 convert the fluorescence, as visible light, into electric charges. Consequently, in a case where radiation 16 passes through the subject 14, the scintillator 74 generates fluorescence depending on the amount of radiation 16 that has passed through the subject 14, and the photodiodes 76 generate electric charges depending on the amount of generated fluorescence. The radiation detector 70 detects the electric charges as electric signals representative of a radiographic image.

Figure 6:
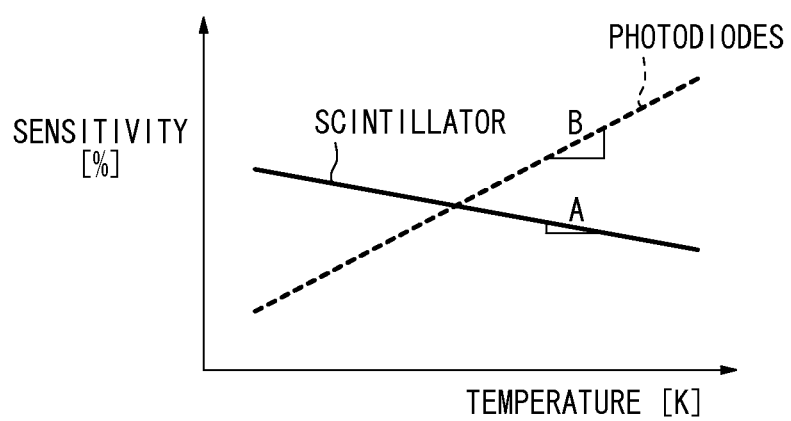
FIG. 6 is a graph showing temperature-dependent rates of change in sensitivity of a scintillator, which undergoes a small sensitivity reduction upon a rise in temperature, and photodiodes, which undergo a large sensitivity increase upon a rise in temperature.

If the scintillator 74 is made of CsI:Tl (cesium iodide with added thallium), then the sensitivity of the scintillator 74 decreases as the temperature of the scintillator 74 rises. In other words, as the amount of radiation 16 that passes through the subject 14 increases, the scintillator 74 increases in temperature and becomes less liable to generate fluorescence commensurate with the increase in the amount of radiation 16 that passes through the subject 14. Conversely, the sensitivity of the photodiodes 76, which may be made of a-Si (amorphous silicon), generally becomes higher as the temperature of the photodiodes 76 rises. In other words, as the amount of fluorescence that is applied to the photodiodes 76 increases, the temperature of the photodiodes 76 increases and the photodiodes 76 become more liable to generate electric charges, which are commensurate with the increase in the amount of fluorescence applied to the photodiodes 76. Therefore, if a scintillator 74, which undergoes a small sensitivity reduction upon a rise in temperature, and photodiodes 76, which undergo a large sensitivity increase upon a rise in temperature are selected, as shown in FIG. 6, then in a case where the radiation detector 70 is at a high temperature, the amount of fluorescence generated by the scintillator 74 is slightly lowered, whereas the amount of electric charge generated by the photodiodes 76 increases significantly. Such an imbalance between the amount of generated fluorescence and the amount of generated electric charge is responsible for generation of artifacts in the captured radiographic image.

As described above, an artifact is generated if a temperature distribution is developed within the plane of the radiation detector 70. Such a temperature distribution is developed by heat, which is transferred from external heat sources to the radiation detector 70, as well as by heat generated by internal heat sources in the housing 58, which accommodates the radiation detector 70 therein. The external heat sources also include the patient, who is held against the electronic cassette 20, and other heating devices that are disposed closely or in contact with the electronic cassette 20. The internal heat sources in the housing 58 include the battery 102, the circuit board 104, the charge amplifier IC 106, and the communication unit 108.

In the radiation detector 70 shown in FIG. 5, the internal heat sources including the battery 102, the circuit board 104, the charge amplifier IC 106, and the communication unit 108 are spaced from the radiation detector 70. If the radiation detector 70 is in the form of a cassette-type DR panel, which can be inserted into a cassette stand for use in a film/screen image capturing process or an image capturing process using an imaging plate, then the housing 58 has a reduced thickness, or stated otherwise, the housing 58 has a limited thickness dimension. Accordingly, the distances between the radiation detector 70 and the internal heat sources in the housing 58 are relatively small, thereby making the radiation detector 70 susceptible to a temperature distribution in the housing 58. Although a heat diffuser or the like may be placed between the radiation detector 70 and the internal heat sources in the housing 58, it is difficult for the heat diffuser to make the temperature distribution fully uniform.

Figure 7:
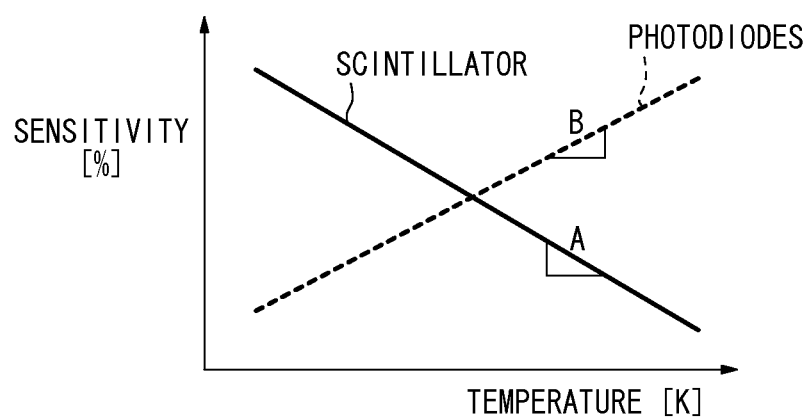
FIG. 7 is a graph showing temperature-dependent rates of change in sensitivity of a scintillator, which undergoes a large sensitivity reduction upon a rise in temperature, and photodiodes, which undergo a large sensitivity increase upon a rise in temperature.

According to the present embodiment, a scintillator 74 and photodiodes 76, which are capable of canceling out respective temperature dependencies in relation to the sensitivity thereof are selected. More specifically, if it is assumed that the temperature-dependent rate of change in sensitivity of the scintillator 74 with respect to radiation 16 is represented by A [%/K], whereas the temperature-dependent rate of change in sensitivity of the photodiodes 76 with respect to visible light is represented by B [%/K], then as shown in FIG. 7, the sum of the temperature-dependent rates of change A and B (A+B) should preferably be close to nil (0). More specifically, the sum of the temperature-dependent rates of change A and B (A+B) should preferably satisfy the following inequality (1):

$$-0.35\ [\%/K] < A+B < 0.35\ [\%/K] \tag{1}$$

The rate A=-0.1 [%/K] implies that the sensitivity drops by 0.1% in a case where the temperature changes by 1 K. Similarly, the rate B =0.1 [%/K] implies that the sensitivity rises by 0.1% in a case where the temperature changes by 1 K.

As the temperature of the radiation detector 70 increases, a reduction in the amount of fluorescence generated by the scintillator 74 is compensated for by an increase in the amount of electric charge generated by the photodiodes 76. Consequently, the photodiodes 76 generate an amount of electric charge commensurate with the amount of radiation 16 that passes through the subject 14, thereby preventing the captured radiographic image from developing artifacts.

As described above, the sensitivity of a general scintillator 74 decreases as the temperature thereof increases, whereas the sensitivity of general photodiodes 76 increases as the temperature thereof increases. Therefore, A<0 and B>0.

The temperature-dependent rate of change A in sensitivity of the scintillator 74 changes depending on the temperature at the time the scintillator 74 is grown as a film during the fabrication process. For example, if a scintillator 74 of CsI:Tl is grown as a film at 700° C., 800° C., and 900° C., respectively, then the temperature-dependent rate of change A in sensitivity of the scintillator 74 is -0.12 [%/K], -0.22 [%/K], and -0.34 [%/K], respectively.

If A = -0.12 [%/K] and B=0.51 [%/K], the sum of A and B (A+B) is 0.39, which does not satisfy inequality (1). If A=-0.22 [%/K] or -0.34 [%/K] and B=0.51 [%/K], the sum of A and B (A+B) is 0.29 or 0.17, which satisfies inequality (1).

Combinations of scintillators 74 and photodiodes 76, which do not satisfy inequality (1) as a result of the calculation of the sum of A and B (A+B), are excluded from use as the scintillator 74 and the photodiodes 76 in the radiation detector 70 according to the present embodiment.

Stated otherwise, the radiation detector 70 according to the present embodiment employs only a combination of a scintillator 74 and photodiodes 76 in which the sum of A and B (A+B) satisfies inequality (1).

Even if the scintillator 74 is made of a material other than CsI:Tl, the sum of A and B (A+B) may be calculated, and the radiation detector 70 may employ a combination of a scintillator 74 and photodiodes 76 having a sum of A and B (A+B)

that satisfies inequality (1), thereby providing the aforementioned temperature-dependent sensitivity for the scintillator 74.

Alternatively, the temperature-dependent rate of change in sensitivity of the photodiodes 76, rather than the scintillator 74, may be varied.

The electronic cassette 20 according to the present embodiment is basically constructed as described above. Operations and advantages of the electronic cassette 20 will be described below.

To acquire a radiographic image of the subject 14, the doctor or radiological technician places the subject 14 so as to lie on the image capturing base 12 (see FIG. 1). Then, the doctor or radiological technician presses the radiation switch 30 in a half stroke, thereby instructing the radiation source controller 28 to prepare the radiation source 26 for emitting radiation 16, and to send a notice signal indicating readiness to apply radiation 16 to the console 22 via a wireless communication link.

In response to the notice signal, the console 22 sends a synchronization control signal for achieving synchronism with application of radiation 16 from the radiation source 26 to the electronic cassette 20 via a wireless communication link. If the controller 40 of the electronic cassette 20 receives the synchronization control signal, the controller 40 displays information, which is indicative of readiness for application of radiation 16, on the display control panel 50 (see FIG. 2). The controller 40 also outputs a sound from the speaker 52 indicative of such information.

Upon the doctor or radiological technician subsequently pressing the radiation switch 30 in a full stroke, the radiation source controller 28 applies radiation 16 from the radiation source 26 to the region to be imaged of the subject 14 for a preset period of time. The radiation source controller 28 may send a notice signal indicative of the start of application of radiation 16 to the console 22 via a wireless communication link, at the same time that radiation 16 starts to be applied. The console 22 transfers the received notice signal to the electronic cassette 20. In response to reception of the notice signal, the controller 40 of the electronic cassette 20 may display information indicative of application of radiation 16 on the display control panel 50, as well as outputting a sound indicative of such information from the speaker 52.

Radiation 16 passes through the region to be imaged of the subject 14 and the irradiated surface 46 and the inner ceiling surface 68 of the electronic cassette 20, and the radiation 16 is applied to the radiation detector 70. Radiation 16 also passes through the photodetector substrate 78 and is applied to the columnar crystalline structure 84 of the scintillator 74.

The columnar crystalline structure 84 emits an amount of fluorescence as visible light, which depends on the amount of radiation 16 applied thereto. The emitted fluorescence travels from the scintillator 74 to the photodetector substrate 78.

The photodiodes 76 of the photodetector substrate 78 generate and store an amount of electric charge depending on the emitted amount of fluorescence, which is applied to the photodetector substrate 78. The controller 40 reads information representative of the electric charges in order to produce a radiographic image of the region to be imaged of the subject 14.

While the above process is repeated, the temperature of the radiation detector 70 increases, thereby reducing the sensitivity of the scintillator 74 and increasing the sensitivity of the photodiodes 76. According to the present invention, a scintillator 74 and photodiodes 76 are selected, the rates of change A and B in sensitivity of which satisfy the above inequality (1). Therefore, the reduction in sensitivity of the scintillator 74 and the increase in sensitivity of the photodiodes 76 cancel each other out, so that the photodiodes 76 generate an amount of electric charge depending on the amount of radiation 16 that has passed through the subject 14.

In this manner, artifacts are prevented from being developed and appearing in the captured radiographic image, and hence diagnostic accuracy based on the radiographic image is not lowered.

According to the present embodiment, as described above, the temperature-dependent rates of change A and B in sensitivity of the scintillator 74 and the photodiodes 76 are set to appropriate values, so as to avoid generation of artifacts in the captured radiographic image. Therefore, the captured radiographic image is clearly visually recognizable, whereby diagnostic accuracy based on the radiographic image is high.

In as much as the reduction in sensitivity of the scintillator 74 and the increase in sensitivity of the photodiodes 76 cancel each other out, even if the temperature distribution of the radiation detector 70 suffers a deviation, for example, in a case where the subject 14 touches the irradiated surface 46 of the electronic cassette 20, artifacts are prevented from being developed in the captured radiographic image due to such a deviation in the temperature distribution. Accordingly, the electronic cassette 20 does not require a heat radiator, and there is no need to generate a correcting program for reducing artifacts which otherwise would be developed in the captured radiographic image. For the reasons discussed above, the electronic cassette 20 is relatively simple in structure.

The above operation sequence is based on the premise that the temperature of the scintillator 74 and the temperature of the photodiodes 76 are substantially identical to each other. The radiographic image capturing system 10 is configured to issue a warning if the temperature difference between the scintillator 74 and the photodiodes 76 exceeds a predetermined threshold value. The temperature of the scintillator 74 and the temperature of the photodiodes 76 can be measured using temperature sensors (not shown), which are associated respectively with the scintillator 74 and the photodiodes 76. The threshold value referred to above is established based on gradients of the temperature-dependencies in sensitivity (i.e., rates of change in sensitivity) of the scintillator 74 and the photodiodes 76.

The radiation detector 70 can be manufactured in the following manner.

First, a scintillator 74 is grown as a film on the scintillator support board 72 using a known film growing process, such as evaporation, chemical vapor deposition (CVD), or the like.

If the temperature at the time the scintillator 74 is grown is too low, then the rate of film growth becomes low. If the temperature at the time the scintillator 74 is grown is too high, then bumps may be formed on the scintillator 74. Bumps on the scintillator 74 tend to cause image defects, which are difficult to correct. To avoid such drawbacks, the temperature at the time the scintillator 74 is grown should preferably be in a range from 750 to 900° C.

The rate of change A in sensitivity of the scintillator 74 differs depending on the film growing process and the film growth temperature, due to different impurity level numbers. Therefore, at this time, the rate of change A in sensitivity of the scintillator 74 should preferably be measured, for example.

Based on the measured rate of change A in sensitivity of the scintillator 74, photodiodes 76 having a rate of change B in sensitivity that satisfies inequality (1) are selected. For example, if the rate of change A in sensitivity of the scintillator 74 grown as a film is −0.22 [%/K], then photodiodes 76 having a rate of change B in sensitivity that is smaller than 0.57 [%/K] and greater than −0.13 [%/K] should be selected. Even if the rate of change A in sensitivity of the scintillator 74 is −0.12 [%/K], a combination that satisfies inequality (1) is obtained by growing photodiodes 76 as a film having a rate of change B in sensitivity that is smaller than 0.47 [%/K] and greater than −0.23 [%/K]. If the scintillator 74 is made of gadolinium oxysulfide (gadolinium oxide sulfur, GOS), then the rate of change A in sensitivity thereof may occasionally be almost nil. In this case, photodiodes 76 may be grown as a film having a rate of change B in sensitivity, which is smaller than 0.35 [%/K] and greater than −0.35 [%/K].

Stated otherwise, according to such a manufacturing method, based on the rate of change A in sensitivity of the scintillator 74, photodiodes 76 are grown as a film having a rate of change B in sensitivity that satisfies inequality (1). In this manner, a combination of a scintillator 74 and photodiodes 76, the rates of change in sensitivity of which cancel each other out, can be obtained.

Then, the scintillator 74 and the photodetector substrate 78 are joined to each other by the first bonding layer 80, thereby producing the radiation detector 70 according to the present embodiment.

The radiation detector 70 then is joined to the inner ceiling surface 68 of the second casing 66 by the second bonding layer 82. The second casing 66, with the radiation detector 70 mounted therein, and the first casing 64 are combined with each other, thereby producing the panel 42. The panel 42 and the controller 40 then are combined to produce the electronic cassette 20.

Conversely, photodiodes 76 are first grown as a film on the photodetector substrate 78, and based on the rate of change B in sensitivity of the photodiodes 76, a scintillator 74 having a rate of change A in sensitivity that satisfies inequality (1) may be selected. For example, if the rate of change B in sensitivity of the photodiodes 76 grown as a film is 0.51 [%/K], then a scintillator 74 having a rate of change A in sensitivity that is greater than −0.86 [%/K] and smaller than −0.16 [%/K] should be grown as a film.

Subsequently, the scintillator 74 and the photodetector substrate 78 may be joined to each other by the first bonding layer 80, thereby producing the radiation detector 70 according to the present embodiment.

The radiation detector 70 may then be joined to the inner ceiling surface 68 of the second casing 66 by the second bonding layer 82. The second casing 66, with the radiation detector 70 mounted therein, and the first casing 64 may be combined with each other, thereby producing the panel 42. The panel 42 and the controller 40 are then combined into the electronic cassette 20.

The present invention is not limited to the embodiment described above, but various changes and modifications may be made to the embodiment without departing from the scope of the invention.

For example, signals may be sent and received via wired communication links such as cables, rather than by the wireless communication links referred to above in the illustrated embodiment.

The scintillator 74 and the photodiodes 76 may be made of any materials, not just CsI:Tl and a-Si, insofar as the rates of change A and B in sensitivity thereof satisfy inequality (1).

Figure 8:
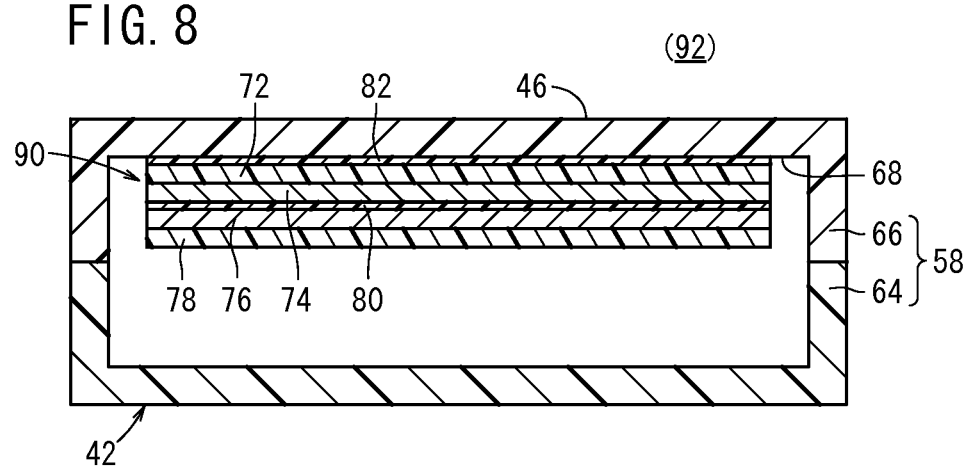
FIG. 8 is a cross-sectional view of an electronic cassette, which serves as a radiographic image capturing apparatus according to another embodiment of the present invention.

As shown in FIG. 8, a radiation detector 90 may include the photodetector substrate 78 having the photodiodes 76, the first bonding layer 80, a scintillator 74, and the scintillator support board 72, such elements being successively arranged in this order upwardly toward the inner ceiling surface 68. The radiation detector 90 may be joined to the inner ceiling surface 68, thereby producing an electronic cassette 92. In FIG. 8, the circuit board support plate 100 (see FIG. 3) as well as various circuits on the circuit board support plate 100 has been omitted from illustration.

Inventive Examples 1 through 3 and Comparative Examples 1 through 3 will be described below.

EXAMPLES

Inventive Example 1

A scintillator 74 made of CsI:Tl was deposited on the scintillator support board 72 by evaporation at 750° C. Photodiodes 76 made of a-Si were deposited on the photodetector substrate 78 by evaporation. The temperature-dependent rates of change A and B in sensitivity of the scintillator 74 and the photodiodes 76 were −0.19 [%/K] and 0.51 [%/K], respectively. The sum of A and B (A+B) was 0.32.

A radiation detector 70 was constructed made up of the scintillator 74 and the photodiodes 76, and the radiation detector 70 was then joined to the inner ceiling surface 68, thereby producing an electronic cassette according to Inventive Example 1.

Inventive Example 2

A radiation detector 70 was constructed in the same manner as Inventive Example 1, except that a scintillator 74 made of CsI:Tl was deposited by evaporation at 800° C., thereby producing an electronic cassette according to Inventive Example 2. The temperature-dependent rates of change A and B in sensitivity of the scintillator 74 and the photodiodes 76 were −0.22 [%/K] and 0.51 [%/K], respectively. The sum of A and B (A+B) was 0.29.

Inventive Example 3

A radiation detector 70 was constructed in the same manner as Inventive Examples 1 and 2, except that a scintillator 74 made of CsI:Tl was deposited by evaporation at 900° C., thereby producing an electronic cassette according to Inventive Example 3. The temperature-dependent rates of change A and B in sensitivity of the scintillator 74 and the photodiodes 76 were −0.34 [%/K] and 0.51 [%/K], respectively. The sum of A and B (A+B) was 0.17.

Inventive Example 4

A radiation detector was constructed in the same manner as Inventive Examples 1 through 3, except that a scintillator made of CsI:Tl was deposited by evaporation at 950° C., thereby producing an electronic cassette according to Inventive Example 4. Temperature-dependent rates of change A and B in sensitivity of the scintillator and the photodiodes were −0.37 [%/K] and 0.51 [%/K], respectively. The sum of A and B (A+B) was 0.14.

Comparative Example 1

A radiation detector was constructed in the same manner as Inventive Examples 1 through 4, except that a scintillator made of CsI:Tl was deposited by evaporation at 700° C., thereby producing an electronic cassette according to Comparative Example 1. The temperature-dependent rates of change A and B in sensitivity of the scintillator and the photodiodes were −0.12 [%/K] and 0.51 [%/K], respectively. The sum of A and B (A+B) was 0.39.

Comparative Example 2

A radiation detector was constructed in the same manner as Inventive Examples 1 through 4, except that a scintillator made of GOS was deposited by evaporation, thereby producing an electronic cassette according to Comparative Example 2. The temperature-dependent rates of change A and B in sensitivity of the scintillator and the photodiodes were −0.03 [%/K] and 0.51 [%/K], respectively. The sum of A and B (A+B) was 0.48.

<Comparison>

Using the electronic cassettes 20 according to Inventive Examples 1 through 4 together with the electronic cassettes according to Comparative Examples 1 and 2, the radiographic image capturing system 10 shown in FIG. 1 was operated to apply radiation 16 to the subject 14 at 25° C. and 35° C., respectively, in order to capture radiographic images. Evaluated levels of visual recognizability of the captured radiographic images, as well as the temperature-dependent rates of change A and B in sensitivity of the scintillators and the photodiodes are tabulated as shown in FIG. 9. In FIG. 9, "o" indicates that density differences were clear and visual recognizability was good, whereas "Δ" indicates that density differences were slightly unclear and visual recognizability was only fair.

In addition, if bumps were formed due to sudden bubbling upon the film growth of CsI:Tl, adverse effects caused by such bumps as image defects on the quality of the captured radiographic images were evaluated. Radiographic images with image defects that were not sufficiently corrected depending on the size and the degree of clustering thereof and which could potentially be recognized visually as image irregularities were marked with "Δ", whereas radiographic images without image defects or with image defects that were not recognized visually after being corrected were marked with "o".

It can be seen from FIG. 9 that the electronic cassettes 20 according to Inventive Examples 1 through 3 were able to produce radiographic images, which were highly visually recognizable and free of image defects, or which were so high in quality that image defects, if any, could be corrected.

Though the image defects in Inventive Example 4 could potentially be recognized visually as image irregularities, there was no problem in practical use.

Although certain preferred embodiments of the present invention have been shown and described in detail, it should be understood that various changes and modifications may be made to the embodiments without departing from the scope of the invention as set forth in the appended claims.

What is claimed is:

1. A radiation detector comprising a scintillator for converting radiation into visible light and photodiodes for converting the visible light into electric charges, wherein:
if it is assumed that a temperature-dependent rate of change in sensitivity of the scintillator with respect to the radiation is represented by A [%/K] and a temperature-dependent rate of change in sensitivity of the photodiodes with respect to visible light is represented by B [%/K], the temperature-dependent rates of change A and B satisfy the following inequality (1):

$$-0.35 \, [\%/K] < A+B < 0.35 \, [\%/K] \qquad (1).$$

2. The radiation detector according to claim 1, wherein A<0 and B>0.

3. The radiation detector according to claim 2, wherein A<−0.2.

4. The radiation detector according to claim 1, wherein the scintillator is made of CsI and the photodiodes are made of amorphous silicon.

5. A method of manufacturing a radiation detector including a scintillator for converting radiation into visible light and photodiodes for converting the visible light into electric charges, comprising the steps of:
measuring a temperature-dependent rate of change in sensitivity of the scintillator with respect to the radiation; and
if it is assumed that the temperature-dependent rate of change in sensitivity of the scintillator with respect to the radiation is represented by A [%/K], selecting, as the photodiodes, photodiodes having a temperature-dependent rate of change B [%/K] in sensitivity with respect to the visible light that satisfies the following inequality (1):

$$-0.35 \, [\%/K] < A+B < 0.35 \, [\%/K] \qquad (1).$$

6. The method according to claim 5, wherein photodiodes with B>0 are selected as the photodiodes if A<0.

7. The method according to claim 6, wherein a scintillator with A<−0.2 is selected as the scintillator.

8. The method according to claim 5, wherein CsI is selected as the material of the scintillator, and amorphous silicon is selected as the material of the photodiodes.

9. The method according to claim 5, wherein the scintillator is grown as a film in a temperature range of 750 to 900° C.

10. A method of manufacturing a radiation detector including a scintillator for converting radiation into visible light and photodiodes for converting the visible light into electric charges, comprising the steps of:
measuring a temperature-dependent rate of change in sensitivity of the photodiodes with respect to the visible light; and
if it is assumed that the temperature-dependent rate of change in sensitivity of the photodiodes with respect to the visible light is represented by B [%/K], selecting, as the scintillator, a scintillator having a temperature-dependent rate of change A [%/K] in sensitivity with respect to the radiation that satisfies the following inequality (1):

$$-0.35 \, [\%/K] < A+B < 0.35 \, [\%/K] \qquad (1).$$

11. The method according to claim 10, wherein a scintillator with A<0 is selected as the scintillator if B>0.

12. The method according to claim 11, wherein a scintillator with A<−0.2 is selected as the scintillator.

13. The method according to claim 10, wherein CsI is selected as a material of the scintillator, and amorphous silicon is selected as a material of the photodiodes.

14. The method according to claim 10, wherein the scintillator is grown as a film in a temperature range of 750 to 900° C.

15. A radiographic image capturing apparatus comprising a housing and a radiation detector accommodated in the housing, the radiation detector including a scintillator for converting radiation into visible light and photodiodes for converting the visible light into electric charges, wherein:
the housing has an irradiated surface facing a radiation source;
if it is assumed that a temperature-dependent rate of change in sensitivity of the scintillator with respect to the radiation is represented by A [%/K] and a temperature-dependent rate of change in sensitivity of the photodiodes with respect to visible light is represented by B [%/K], the temperature-dependent rates of change A and B satisfy the following inequality (1):

$$-0.35\ [\%/K] < A+B < 0.35\ [\%/K] \qquad (1);$$

and the radiation detector is mounted on a surface of the housing that is opposite to the irradiated surface.

16. The radiographic image capturing apparatus according to claim 15, wherein A<0 and B>0.

17. The radiographic image capturing apparatus according to claim 16, wherein A<−0.2.

18. The radiographic image capturing apparatus according to claim 15, wherein the scintillator is made of CsI and the photodiodes are made of amorphous silicon.

* * * * *